United States Patent
Thorball et al.

(10) Patent No.: US 6,283,294 B1
(45) Date of Patent: Sep. 4, 2001

(54) ENCLOSED LIVING CELL DISPENSING TUBE

(75) Inventors: Jørgen Thorball, Virum (DK); Otto Skolling, Täby (SE); Ivan A. Casas, Raleigh, NC (US)

(73) Assignee: Biogaia Biologics AB, Gothenburg (SE)

( * ) Notice: Subject to any disclaimer, the term of this patent is extended or adjusted under 35 U.S.C. 154(b) by 0 days.

(21) Appl. No.: 09/387,947

(22) Filed: Sep. 1, 1999

(51) Int. Cl.[7] .............................. A61B 19/02; A61J 15/00; A01N 63/00; A61M 37/00
(52) U.S. Cl. .......................... 206/438; 239/33; 424/439; 424/93.45; 426/85; 604/85; 604/518
(58) Field of Search ..................................... 206/219, 484, 206/438; 239/33; 426/85, 87, 115; 424/439, 473, 93.45; 604/518, 85

(56) References Cited

U.S. PATENT DOCUMENTS

| | | | |
|---|---|---|---|
| 1,996,203 | * | 4/1935 | Hollingsworth ........................ 426/85 |
| 3,099,565 | | 7/1963 | Neuhauser . |
| 3,615,595 | * | 10/1971 | Guttag ..................................... 426/85 |
| 3,717,476 | * | 2/1973 | Harvey .................................... 426/85 |
| 3,957,202 | | 5/1976 | Hornsby, Jr. . |
| 4,151,916 | * | 5/1979 | Eriksson ................................ 206/484 |
| 4,387,809 | | 6/1983 | Botzler . |
| 4,518,696 | * | 5/1985 | Gehrman et al. ............. 474/93.45 X |
| 4,986,451 | | 1/1991 | Lowe . |
| 5,076,425 | | 12/1991 | Plone . |
| 5,190,755 | * | 3/1993 | Molin et al. ........................ 426/18 X |
| 5,334,348 | * | 8/1994 | Saito et al. ......................... 239/33 X |
| 5,589,368 | * | 12/1996 | Allen et al. ...................... 424/439 X |
| 5,681,564 | * | 10/1997 | Saulson ............................... 426/85 X |
| 5,718,681 | * | 2/1998 | Manning ............................ 239/33 X |
| 5,728,380 | * | 3/1998 | Allen et al. ...................... 424/439 X |
| 5,820,023 | * | 10/1998 | Kristensson ............................. 239/33 |
| 5,837,238 | * | 11/1998 | Casas et al. ........................ 424/93.45 |
| 5,910,321 | * | 6/1999 | Wong et al. .......................... 424/473 |
| 6,060,050 | * | 5/2000 | Brown et al. ................. 424/93.45 X |

FOREIGN PATENT DOCUMENTS

| PCT/AU97/ 00680 | 4/1998 | (AU) . |
|---|---|---|
| 0 111 188 | 11/1983 | (EP) . |

\* cited by examiner

*Primary Examiner*—Bryon P. Gehman
(74) *Attorney, Agent, or Firm*—Lynn E. Barber

(57) ABSTRACT

A dispensing tube containing a selected material, such as bacterial cells or other additive, on the inside of the tube. The tube is wrapped and sealed in an outer watertight envelope until time for usage. At the time of usage the outer envelope is taken away and when the tubular device penetrates a solution container such as a beverage or an enteral solution, the selected material is added to the solution while the solution flows through the tube.

37 Claims, 3 Drawing Sheets

ENCLOSED LIVING CELL DISPENSING TUBE

BACKGROUND OF THE INVENTION

1. Field of the Invention

This invention relates to devices used to add components to packaged liquids, such as beverages.

2. Description of the Related Art

In the pharmaceutical and food industry it is well-known that addition of health-promoting bacteria (e.g. probiotic bacteria such as lactic bacteria or bifido bacteria) allows people to maintain a proper gut function. However, it has been difficult and relatively expensive to have an acceptable shelf life of a mixed product that contains these bacteria. The problem has been that such drinks or enteral solutions go through a thermal sterilization or are aseptically filled in presterilized containers, thus killing or removing any live bacteria added during the production process. If the bacteria are added directly into the solution during the production/filling process and after sterilization, the bacteria are likely to be re-activated by the presence of water, and would accordingly multiply and finally die within a few weeks or months after production. The metabolites of the bacteria might also change the solution taste and nutritional value.

To avoid the interaction between the solution and the bacteria prior to ingestion, special delivery systems have been integrated into solution containers like e.g., Tetrabrik or Pet bottles (see, for example, co-pending PCT application PCT/US98/21490). Since these delivery systems are more or less an integral part of the packaging, the producer cannot choose during or after production to have some of the products have the delivery system and some not to have it.

Attempts to solve these problems include the use of tubular devices, such as telescopic packaging infusion units formed as tubes from a liquid impermeable material. For example U.S. Pat. No. 3,102,465 and PCT/AAU97/00680 disclose straw-shaped units that can be opened so that the ingredient contained in the unit can be dispensed. A number of patents, for example, U.S. Pat. Nos. 4,860,929 and 4,986,451, provide tubular devices closed on both ends and having perforations along the sides to allow granular material to be released and dissolved in contact with water or another solvent. Other methods of adding a material to a liquid by means of a straw-device include coating the outside of one end of a straw with a flavored coating that dissolves when the straw is placed in a liquid or making the end of a straw in the form of a spoon made of a soluble substance. Other straw-shaped novelty inventions provide straws with internal or external decorative features and substances.

It is therefore an object of the invention to provide a simple low-cost and consumer-friendly system to protect bacteria for an extended term at room temperature, and have a ready-to-use system for the patient or the user after this extended term.

It is a further object to provide a device that enable addition to drinks of an ingredient such as a probiotic microorganism, using a straw that the consumer can then use to sip the drink.

It is a further object of the invention to provide a means of adding probiotic bacteria or other additives to beverages such as dairy products or soft drinks or to enteral solutions which have been through an aseptic or sterile treatment, e.g., sterile filtration, irradiation or thermal sterilization.

It is a further object of the invention to provide a device for adding components to beverages which has a water and moisture tight container until it is opened and ready for use.

It is a further object of the invention to provide a means for long-term storage of health promoting bacteria.

It is a further object of the invention to provide a new delivery system for other moisture-sensitive or oxygen-sensitive components, such as certain amino acids, peptides, nucleotides, vitamins, hormones and proteins.

Other objects and advantages will be more fully apparent from the following disclosure and appended claims.

SUMMARY OF THE INVENTION

The invention herein is a dispensing tube containing a selected material, such as bacterial cells or other additive, on the inside of the tube. The tube is wrapped and sealed in an outer watertight envelope until time for usage. At the time of usage the outer envelope is taken away and when the tubular device penetrates a solution container such as a beverage or an enteral solution, the selected material is added in the desired amount to the solution while the solution flows through the tube.

Other objects and features of the inventions will be more fully apparent from the following disclosure and appended claims.

DETAILED DESCRIPTION OF THE INVENTION AND PREFERRED EMBODIMENTS THEREOF

The present invention is a dispensing tube having a structure similar to that of a drinking straw. The dispensing tube is impermeable to liquids and open at both ends for the purpose of delivering the solution through the device normally by sucking. In the preferred embodiment, a selected material, such as a suspension of typically probiotic microorganism, for example, lactic bacteria or bifidus bacteria, is added to the dispensing tube as described below. In the preferred embodiments of the invention, during production of the tube of the invention, a second tube delivers the selected material into the dispensing tube. The tube is then placed into a water-resistant outer envelope using a packaging machine as is known in the art. The materials used in the manufacture of the invention, in particular, the dispensing tube and the outer envelope, must be capable of protecting the bacteria or other selected material from contamination and moisture for periods of up to 12 months storage at room temperature. The tube material must also be able to withstand the suspension media used for the bacteria or whatever other selected material is used.

Figure 1:
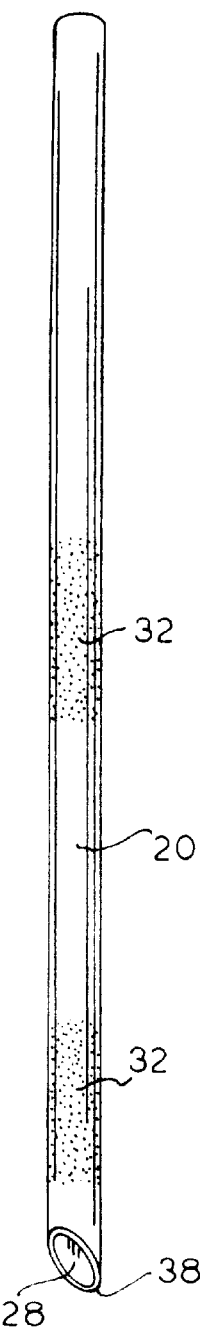
FIG. 1 is a perspective view of a first embodiment of the tube of the invention.
Figure 2:
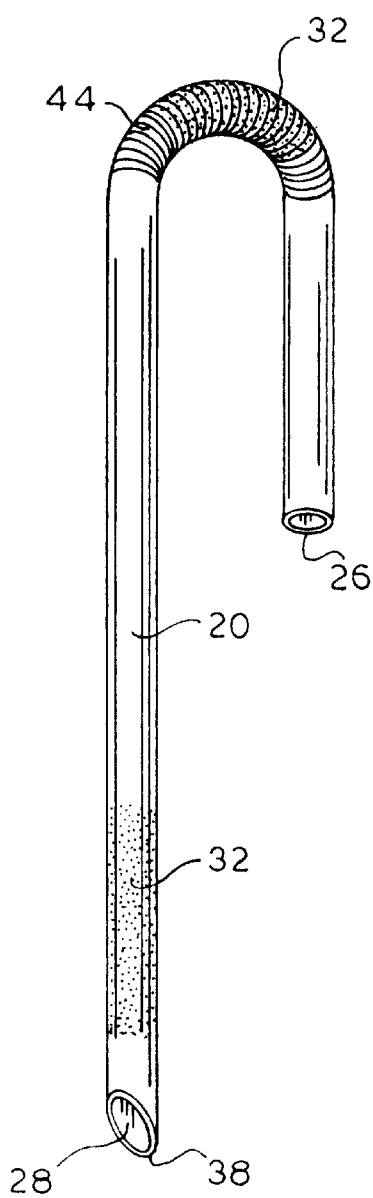
FIG. 2 is a perspective view of a second embodiment of the tube of the invention.
Figure 3:
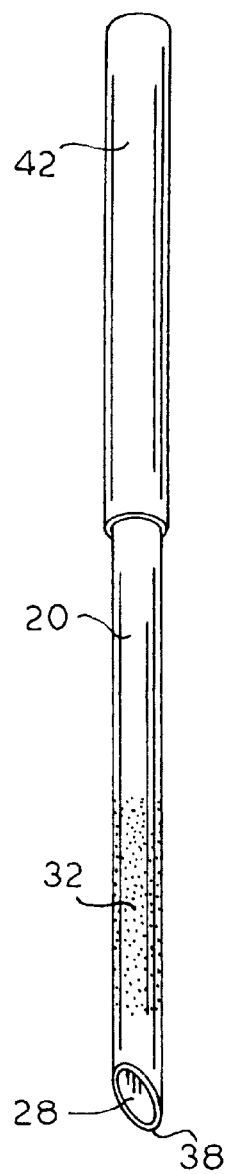
FIG. 3 is a perspective view of a third embodiment of the tube of the invention.
Figure 4:
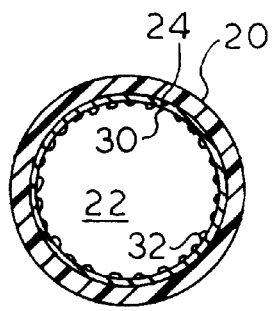
FIG. 4 is a cross-section of a portion of the tube that has an adherent selected material inside the tube.
Figure 5:
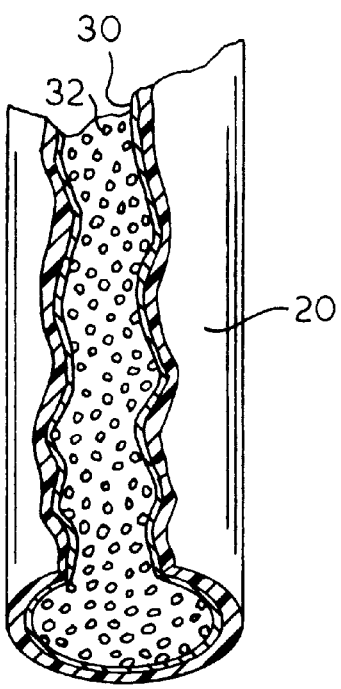
FIG. 5 is a partial view of a partially sectioned tube end showing the location of adherent selected material.
Figure 7:
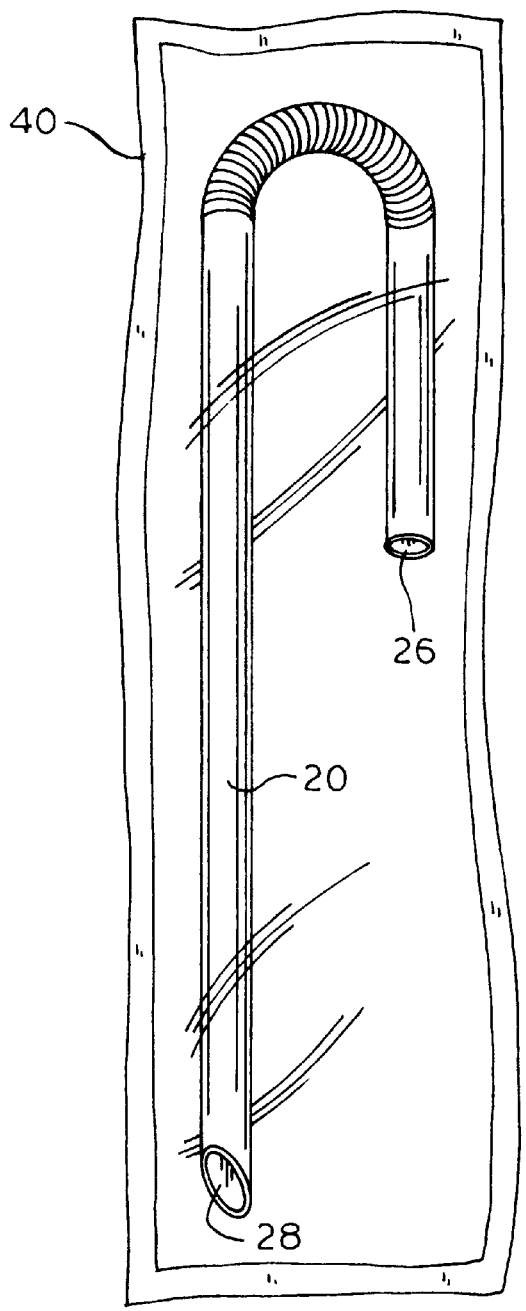
FIG. 7 is a perspective view of the device of the invention packaged in an envelope.
Figure 6A:
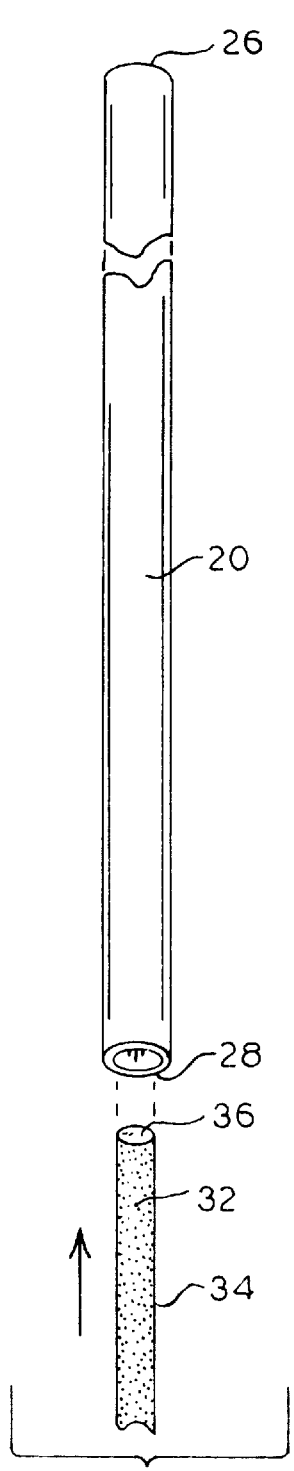
FIGS. 6A–6C depict a coated second tube prior to insertion in the impermeable tube (FIG. 6A); the coated second tube inserted partway into the impermeable tube (FIG. 6B); and the rotation of the coated second tube end and dislodgment of selected material inside the impermeable tube.
Figure 6B:
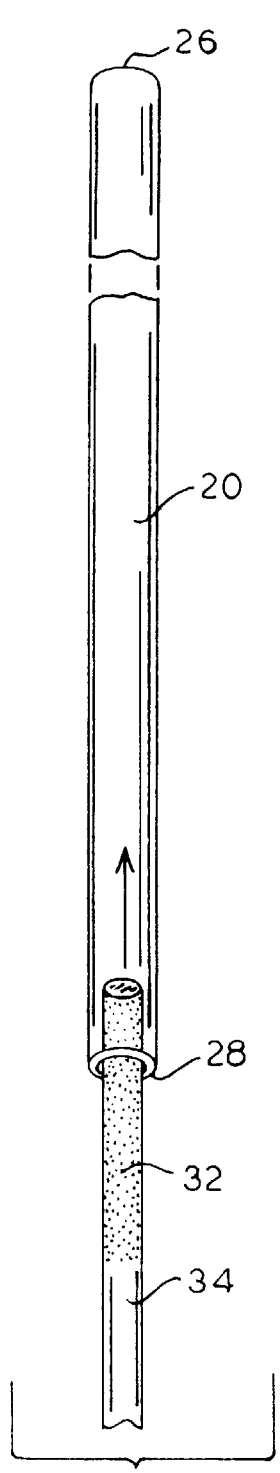
Figure 6C:
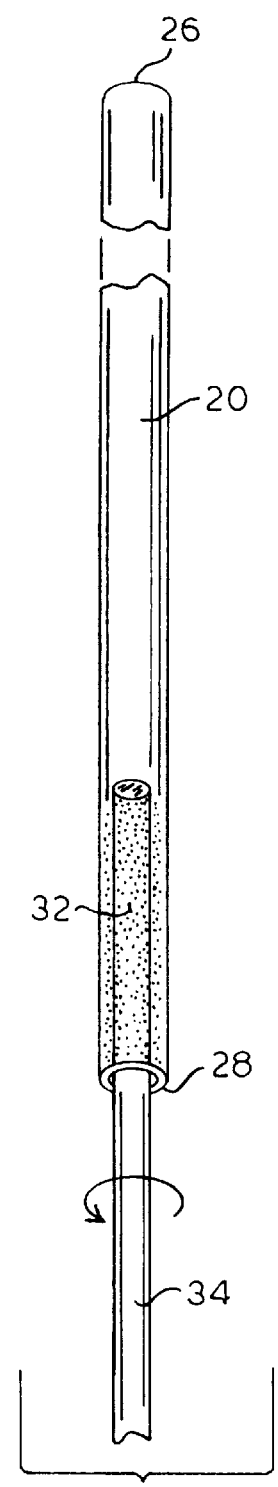

Referring to the figures, the invention herein is a dispensing tube for dispensing a selected material into a liquid, comprising a liquid impermeable tube 20 having an open bore 22 surrounded by an inner tube wall 24. Bore 22 is open at both an upper end 26 and a lower end 28 of the tube as shown in FIGS. 1–3; in other words, the tube is not closed at either end. Tube 20 is preferably of a size and structure as is known with drinking straws, such as the straws that are used with boxed individual drink cartons, and is preferably formed from a synthetic polymeric material such as polyethylene or polypropylene, or from paper with an internal coating of a wax material. Preferred dimensions range from a width of 0.2–20 mm and a length of 50–500 mm. The tube may be a commercial drinking straw.

Thus, if tube 20 is to be used with a standard drink box having a puncturable opening, the lower end 28 of the tube is preferably a pointed end as shown in FIGS. 1–3 and 7. Other dispensing tubes that may be used in the invention include those with bellows 44 as is known in the art (FIG. 2). Since straws used in Japan often have an outer tube into which the drinking straw telescopes, the invention herein also include an embodiment having an outer tube 42 as shown in FIG. 3.

It is important that tube 20 have the capability to hold the suspension, and to hinder the suspension from unintentional leakage out of the tube 20. This is accomplished either by surface tension through appropriate selection of the material of which the tube is made or by treatment of tube 20. It also could be done by altering the viscosity of the suspension. Although not required for the invention, in the preferred embodiments of the invention, the inner wall of the tube is coated or is otherwise surface-modified to give a higher surface tension. Thus, in the preferred embodiments, the invention further includes a coating material 30 for holding a suspension of the selected material 32 within the open bore 22 adherent to the inner tube wall 24. This coating material 30 may comprise any coating substance which is non-toxic to humans and to the bacteria to be added to the tube, and which adheres to the inner tube wall 24, for example, a dietary oil such as corn oil or a wax. The coating material may be applied in a number of ways, for example, by insertion of an elongated stick or other device coated with the substance, with a tubular filling device, or by spraying the inside of tube 20.

The bacteria or additive may be applied with the coating substance, or be separately applied to selected positions inside the tube (for example, a small drop of about 10 $\mu$l) evenly sprayed all over the inside of the tube after coating the inside of tube 20. The pattern and extent of distribution of the additive inside tube 20 may be determined by the nature of the additive and the intended use. Thus, for an easily soluble additive, even distribution is less critical. If the additive dissolves quickly and is at the distal end of tube 20, it may be desirable to position the additive close to the distal end, so that the additive becomes quickly dispersed in the solution in the container. Another reason to position the additive at the distal end is when the additive has an unpleasant taste, and it is desired to maximally dilute the additive before it is consumed. Alternatively, when the additive has a pleasant taste, it may be positioned at the upper end to increase the good taste of the drink. To minimize exposure of an oxygen-sensitive additive, the additive may be placed in the inside tube 20 in the form of a droplet, which would have less surface area than an evenly dispersed material inside the tube 20.

Preferably the selected material 32 that is to be dispensed from the dispensing tube 20 comprises lyophilized cells of one or more probiotic microorganisms, such as various Lactobacillus or Bifidobacteria strains. Depending on the type of additive being added to tube 20, the suspension containing the additive may need to specially treated to optimize shelf stability and appropriate retention in, and release from, tube 20. For bacteria, the suspension containing the bacteria should not contain a significant amount of water, and should be fairly resistant to oxidation. The suspension should dissolve or release or carry the additive, such as bacteria, into the fluid that is being consumed, at typical use temperatures (e.g., 0° C.–40° C.). Thus, for a number of additives such as bacterial additives, the dried additive is preferably granulized into a very fine powder to insure solubility and even distribution in the solution.

The bacterial suspension or other additive to be contained in the device is preferably prepared in a sufficiently concentrated formulation so that surface tension/adhesion withholds the suspension in the tube. The concentration of the suspension is optimized to give a good ratio between volume and number of bacteria per ml. Preferably the concentration of bacteria is not lower then 1% in the suspension. The cells are preferably mixed directly into the suspending liquid under a nitrogen protective flow to reduce vapor and oxygen presence. Although cells of bacteria would not be visible to the naked eye, the selected material 32 is depicted in the figures as small dots, or as small circles, to show their position (e.g., in FIGS. 1–4 and FIG. 5, respectively).

Other selected materials that could be added to liquids using the device of the invention include vitamins, colorants, minerals, trace elements, homeopathic medicines, drugs, enzymes and the like.

The selected material 32, such as bacterial cells, is preferably added to the tube 20 by providing a second tube 34 having a smaller outer diameter than the inner diameter of the liquid impermeable tube and preferably having a closed end 36 as shown in FIGS. 6A–6C. The closed end 36 is coated externally with the selected material 32 as shown in FIG. 6A, which adhere by surface tension and/or by use of an adhesive material as is known in the art. Then the coated closed end 36 is inserted into the bore 22 at the lower end 28 of the liquid impermeable tube 20 which has been treated in part or entirely with the coating material 30 (FIG. 6B). The closed end 36 is moved, such as being rotated, against the coating material, thereby dislodging selected material that then adheres to the coating on the inner wall (FIG. 6C).

The tube 20 is preferably packaged in a flexible, essentially water vapor tight envelope 40 enclosing the tube 20 as shown in FIG. 7. The outer envelope must be substantially impermeable to water vapor and should have sufficient flexibility and toughness to prevent unintentional puncture, and is preferably made of flexible polymeric material or an aluminum foil, coated on a polymeric film. In all cases the envelope construction is made in such a way that when sealed, water and moisture are prevented from entering the tube device. The material should also be easy to tear open at the point of use. The envelope 40 is preferably made of a polyolefinic material coated with aluminum or of a synthetic polymer as is known in the art with a low water permeation rate. A preferred material for the outer envelope is a polyethylene or polypropylene, including both homopolymers and copolymers of these polymer families, with an aluminum layer as an outer layer. If a transparent envelope 40 is desired, the polyethylene/polypropylene structure may have outer layer comprising a polymer of ethyl vinyl alcohol or poly-vinylidene chloride. Alternatively, polyethylene and/or polypropylene may be used without an aluminum layer if there is not a need for protection from oxygen. Those of ordinary skill in the art may substitute other suitable packaging material.

To use the impermeable tube 20, it is removed from envelope 40, and inserted into a chosen liquid container by either lowering it through an opening in the container as is done with standard straws, or by puncturing a puncturable port on the container as is done with juice cartons. The port of the container, such as a juice box, to which the bacteria are to be added (not shown) may be protected by for instance a puncturable aluminum foil as is known in the art that will make it possible to add bacteria to an aseptic filled or a thermally sterilized solution. At the time of the straw's penetration of the container, for example, of an enteral product, a dairy product, a soft drink or some other type of solution or mixture, the bacteria are integrated into the solution, giving a desirable dose of bacteria in the product. Once the lower end 28 of the tube is immersed in the liquid and the selected material 32 is removed from the inner tube wall 24 and mixed with the liquid by drawing the liquid through the bore from the lower end to the upper end and into the mouth.

The envelope 40 containing the tube 20 can be sold separately from the beverage or other fluid containers, or can be attached to the container, for example, by adhesives as is known in the art for drinking container straws. Thus, tube 20 containing the selected material and in envelope 40 could easily be attached onto every type of package containing solutions where addition of the selected material would be suitable.

While the invention has been described with reference to specific embodiments, it will be appreciated that numerous variations, modifications, and embodiments are possible, and accordingly, all such variations, modifications, and embodiments are to be regarded as being within the spirit and scope of the invention.

What is claimed is:

1. A device for dispensing living cells of a probiotic microorganism into a liquid. comprising:
    (a) a liquid impermeable dispensing tube having an open bore being surrounded by an inner tube wall and extending from an open upper end of the tube to an open lower end of the tube;
    (b) a coating material on a portion of the inner tube wall, said coating material selected from the group consisting of oils and waxes and holding a suspension of the living cells of the probiotic microorganism for long-term storage within the open bore adherent to the inner tube wall; and
    (c) a flexible, essentially water vapor tight envelope enclosing the tube for long-term storage and to protect the living cells of the probiotic microorganism from moisture;
wherein the living cells of the probiotic microorganism may be removed from the inner tube wall and mixed with the liquid by placing the open lower end of the tube in the liquid and drawing the liquid through the bore.

2. The device of claim 1, wherein the probiotic microorganism comprises Lactobacillus.

3. The device of claim 1, wherein the cells of a probiotic microorganism comprise a suspension of lyophilized live bacteria.

4. The device of claim 3, in which the concentration of live bacteria at the point of use is at least 1% of the suspension when the device is manufactured.

5. The device of claim 1, wherein the viscosity of the suspension is modified to provide maximum adherence of the suspension to the device.

6. The device of claim 1, wherein the tube comprises a bellows portion.

7. The device of claim 1, wherein the tube telescopes into an outer tube.

8. The device of claim 1, wherein the tube is made from a synthetic polymer material.

9. The device of claim 1, wherein the tube is made from paper with an internal coating of a wax material.

10. The device of claim 1, wherein the tube has a diameter ranging from 0.2–20 mm and a length of 50–500 mm.

11. The device of claim 1, wherein the tube is a commercial drinking straw.

12. The device of claim 1, wherein the open bore of the tube has been surface modified to give a higher surface tension.

13. The device of claim 1, wherein the envelope is made of a polyolefinic material coated with aluminum.

14. The device of claim 1, wherein the envelope is made of a synthetic polymer with a low water permeation rate.

15. The device of claim 1, wherein the suspension of cells is distributed along the full length of the inner tube wall.

16. The device of claim 1, wherein the suspension of cells is primarily placed at the lower end of the tube.

17. The device of claim 1, wherein the coating material comprises a dietary oil.

18. The device of claim 1, wherein the envelope comprises an aluminum layer.

19. A method of making a device for dispensing living cells of a probiotic microorganism into a liquid, comprising:
    (a) providing a liquid impermeable dispensing tube having an open bore being surrounded by an inner tube wall and extending from an open upper end of the tube to an open lower end of the tube;
    (b) coating a portion of the inner tube wall within the open bore with a coating material selected from the group consisting of oils and waxes and holding a suspension of the living cells of the probiotic microorganism for long-term storage so that the coating material containing the living cells adheres to the inner tube wall; and
    (c) providing a flexible, essentially water vapor tight envelope enclosing the tube for long-term storage and to protect the living cells of the probiotic microorganism from moisture;
wherein the living cells of the probiotic microorganism may be removed from the inner tube wall and mixed with the liquid by placing the open lower end of the tube in the liquid and drawing the liquid through the bore.

20. The method of claim 19, wherein the inner tube wall is coated with the cells of the probiotic microorganism by insertion of a second tube that has a coating of the cells of the probiotic microorganism into the lower end of the dispensing tube.

21. The method of claim 19, wherein the probiotic microorganism comprises Lactobacillus.

22. The method of claim 19, wherein the cells of the probiotic microorganism comprise a suspension of lyophilized live bacteria.

23. The method of claim 22, in which the concentration of live bacteria at the point of use is at least 1% of the suspension when the device is manufactured.

24. The method of claim 19, wherein providing the liquid impermeable dispensing tube comprises providing a tube comprising a bellows portion.

25. The method of claim 19, wherein providing the liquid impermeable dispensing tube comprises providing a tube that telescopes into an outer tube.

26. The method of claim 19, wherein providing the liquid impermeable dispensing tube comprises providing a tube made from a synthetic polymer material.

27. The method of claim 19, wherein providing the liquid impermeable dispensing tube comprises providing a tube made from paper with an internal coating of a wax material.

28. The method of claim 19, wherein providing a liquid impermeable dispensing tube comprises providing a tube having a diameter ranging from 0.2–20 mm and a length of 50–500 mm.

29. The method of claim 19, wherein providing a liquid impermeable dispensing tube comprises providing a commercial drinking straw.

30. The method of claim 19, further comprising surface-modification of the open bore of the tube to give a higher surface tension.

31. The method of claim 19, wherein providing the flexible, essentially water vapor tight envelope enclosing the tube comprises providing a polyolefinic material coated with aluminum.

32. The method of claim 19, wherein providing the flexible, essentially water vapor tight envelope enclosing the tube comprises providing an envelope made of a synthetic polymer with a low water permeation rate.

33. The method of claim 19, wherein coating a portion of the inner tube wall comprises distributing the cells along the full length of the inner tube wall.

34. The method of claim 19, wherein coating a portion of the inner tube wall comprises distributing the suspension of cells at the lower end of the tube.

35. The method of claim 19, further comprising modifying the viscosity of the suspension to provide maximum adherence of the suspension to the device.

36. The method of claim 19, wherein the coating material comprises a dietary oil.

37. The method of claim 19, wherein the envelope comprises an aluminum layer.